United States Patent [19]

Smith et al.

[11] Patent Number: 5,895,377

[45] Date of Patent: *Apr. 20, 1999

[54] VALVE SYSTEM FOR CANNULA ASSEMBLY

[75] Inventors: Robert C. Smith, Danbury; Peter W. J. Hinchliffe, New Haven; James Correia, Shelton; Martin J. Nohilly, Trumbull; Kurt Azarbarzin, Ridgefield; Richard D. Gresham, Monroe, all of Conn.

[73] Assignee: United States Surgical Corporation, Norwalk, Conn.

[ * ] Notice: This patent is subject to a terminal disclaimer.

[21] Appl. No.: 08/802,188

[22] Filed: Feb. 18, 1997

Related U.S. Application Data

[63] Continuation of application No. 08/287,395, Aug. 8, 1994, Pat. No. 5,603,702.

[51] Int. Cl.$^6$ .............................. A61M 5/00; A61M 5/14
[52] U.S. Cl. .................... 604/256; 604/167; 251/149.1
[58] Field of Search .............................. 604/158, 164, 604/167, 169, 256, 264; 285/302; 251/149.1–149.3

[56] References Cited

U.S. PATENT DOCUMENTS

| | | |
|---|---|---|
| 2,797,837 | 7/1957 | Roberts . |
| 3,197,173 | 7/1965 | Taubenheim . |
| 3,473,779 | 10/1969 | Gustafson et al. . |
| 3,875,938 | 4/1975 | Mellor . |
| 3,970,089 | 7/1976 | Shice . |
| 3,977,400 | 8/1976 | Moorehead . |
| 4,000,739 | 1/1977 | Stevens . |
| 4,177,814 | 12/1979 | Knepshield et al. . |
| 4,233,982 | 11/1980 | Bauer et al. . |
| 4,240,411 | 12/1980 | Hosono . |
| 4,243,034 | 1/1981 | Brandt . |
| 4,338,934 | 7/1982 | Spademan . |
| 4,379,458 | 4/1983 | Bauer et al. . |
| 4,424,833 | 1/1984 | Spector et al. . |
| 4,430,081 | 2/1984 | Timmermans . |
| 4,512,766 | 4/1985 | Vailancourt . |
| 4,531,937 | 7/1985 | Yates . |

FOREIGN PATENT DOCUMENTS

| | | |
|---|---|---|
| 29864 | 6/1981 | European Pat. Off. . |
| 054728 | 6/1982 | European Pat. Off. . |
| 0150666 | 8/1985 | European Pat. Off. . |
| 0323018 | 7/1989 | European Pat. Off. . |
| 344907 | 12/1989 | European Pat. Off. . |
| 350291 | 1/1990 | European Pat. Off. . |
| 370720 | 5/1990 | European Pat. Off. . |
| 0517248 | 12/1992 | European Pat. Off. . |
| 0627233 | 12/1994 | European Pat. Off. . |
| 2845643 | 4/1980 | Germany . |
| 3042229 | 5/1982 | Germany . |
| 3242870 | 6/1983 | Germany . |
| 1199498 | 6/1970 | United Kingdom . |
| 2019219 | 10/1979 | United Kingdom . |
| 2063679 | 6/1981 | United Kingdom . |
| WO9407552 | 4/1994 | WIPO . |

*Primary Examiner*—Ronald Stright, Jr.

[57] ABSTRACT

Valve assembly for sealed reception of an elongated object includes a valve body having at least one opening configured and dimensioned to permit entry of an elongated object and defining a central longitudinal axis, an elongated seal member formed of a resilient material and defining an aperture in general alignment with the opening of the valve body whereby the aperture is configured and dimensioned such that insertion of the object into the aperture causes the resilient material defining the aperture to resiliently engage the outer surface of the object in a substantially fluid flight manner, and at least one elongated guard member disposed within the seal member in supporting contact with the inner surface thereof. The guard member is positioned to engage the elongated object upon at least partial insertion of the elongated object into the valve body. The guard member includes at least a first substantially rigid portion adapted to be displaced relative to the longitudinal axis to facilitate expansion of the aperture of the seal member upon entry of the object therein and a second portion having less rigidity than the first portion of the guard member to enhance passage of the elongated object through the valve body.

10 Claims, 13 Drawing Sheets

U.S. PATENT DOCUMENTS

| | | |
|---|---|---|
| 4,535,773 | 8/1985 | Yoon . |
| 4,569,502 | 2/1986 | Elliott . |
| 4,580,573 | 4/1986 | Quinn . |
| 4,609,300 | 9/1986 | Robert . |
| 4,610,665 | 9/1986 | Matsumoto et al. . |
| 4,610,674 | 9/1986 | Suzuki et al. . |
| 4,611,785 | 9/1986 | Steer . |
| 4,626,245 | 12/1986 | Weinstein . |
| 4,629,450 | 12/1986 | Suzuki et al. . |
| 4,634,432 | 1/1987 | Kocak . |
| 4,654,030 | 3/1987 | Moll et al. . |
| 4,655,752 | 4/1987 | Honkanen et al. . |
| 4,673,393 | 6/1987 | Suzuki et al. . |
| 4,683,916 | 8/1987 | Raines . |
| 4,759,751 | 7/1988 | Gabel et al. . |
| 4,798,594 | 1/1989 | Hillstead . |
| 4,813,938 | 3/1989 | Raulerson . |
| 4,842,591 | 6/1989 | Luther . |
| 4,857,062 | 8/1989 | Russell . |
| 4,874,377 | 10/1989 | Newgard et al. . |
| 4,895,346 | 1/1990 | Steigerwald . |
| 4,909,798 | 3/1990 | Fleischbacker et al. . |
| 4,917,668 | 4/1990 | Haindl . |
| 4,929,235 | 5/1990 | Merry et al. . |
| 4,935,010 | 6/1990 | Cox et al. . |
| 4,960,259 | 10/1990 | Sunnanuader et al. . |
| 4,960,412 | 10/1990 | Fink . |
| 4,966,588 | 10/1990 | Rayman et al. . |
| 4,978,341 | 12/1990 | Neiderhauser . |
| 5,000,745 | 3/1991 | Guest et al. . |
| 5,006,114 | 4/1991 | Rogers et al. . |
| 5,009,391 | 4/1991 | Steigerwald . |
| 5,053,014 | 10/1991 | Van Hevgten . |
| 5,092,857 | 3/1992 | Fleischhacker . |
| 5,098,393 | 3/1992 | Amplatz et al. . |
| 5,112,321 | 5/1992 | Hiltebrandt . |
| 5,127,626 | 7/1992 | Hilal et al. . |
| 5,156,596 | 10/1992 | Balbierz et al. . |
| 5,161,773 | 11/1992 | Tower . |
| 5,167,636 | 12/1992 | Clement . |
| 5,180,373 | 1/1993 | Green et al. . |
| 5,197,955 | 3/1993 | Stephens et al. . |
| 5,205,831 | 4/1993 | Ryan et al. . |
| 5,209,737 | 5/1993 | Ritchart et al. . |
| 5,211,634 | 5/1993 | Vaillancourt . |
| 5,242,412 | 9/1993 | Blake, III . |
| 5,256,150 | 10/1993 | Quiachon et al. . |
| 5,300,033 | 4/1994 | Miller . |
| 5,312,362 | 5/1994 | Pfolsgref et al. . |
| 5,312,363 | 5/1994 | Ryan et al. . |
| 5,342,315 | 8/1994 | Rowe et al. . |
| 5,350,364 | 9/1994 | Stephens et al. . |
| 5,385,553 | 1/1995 | Hart et al. ............................ 604/167 |
| 5,460,616 | 10/1995 | Weinstein et al. . |
| 5,492,304 | 2/1996 | Smith et al. ........................ 251/149.1 |
| 5,496,280 | 3/1996 | Vandenbroek et al. ................ 604/167 |
| 5,603,702 | 2/1997 | Smith et al. ............................ 604/256 |

VALVE SYSTEM FOR CANNULA ASSEMBLY

This is a continuation of U.S. application Ser. No. 08/287,395, filed Aug. 8, 1994, now U.S. Pat. No. 5,603,702.

BACKGROUND

1. Technical Field

The present disclosure relates to valve systems of the type adapted to allow the introduction of a surgical instrument into a patient's body. In particular, the disclosure relates to a valve system to be used in combination with a cannula where the cannula is intended for insertion into a patient's body and an instrument is inserted into the patient's body through the cannula.

2. Background Of Related Art

Laparoscopic procedures are performed in the interior of the abdomen through a small incision, e.g., through narrow endoscopic tubes or cannulas inserted through a small entrance incision in the skin. Minimally invasive procedures are performed elsewhere in the body, e.g., in the chest, and are often generally referred to as "endoscopic" procedures. Minimally invasive or endoscopic procedures generally require that any instrumentation inserted into the body be sealed, i.e. provisions must be made to ensure that gases do not enter or exit the body through the endoscopic incision as, for example, in surgical procedures in which the surgical region is insufflated. Moreover, endoscopic procedures often require the surgeon to act on organs, tissues, and vessels far removed from the incision, thereby requiring that any instruments used in such procedures be relatively long and narrow.

For such procedures, the introduction of a tube into certain anatomical cavities such as the abdominal cavity is usually accomplished by use of a system incorporating a trocar and cannula assembly. A cannula assembly is formed of a cannula attached to a cannula housing which generally includes valve assembly adapted to maintain a seal across the opening of the valve assembly both with and without an instrument inserted therethrough. Since the cannula is in direct communication with the internal portion of the valve assembly, insertion of the cannula into an opening in the patient's body so as to reach the inner abdominal cavity should be adapted to maintain a fluid tight interface between the abdominal cavity and the outside atmosphere.

Since minimally invasive surgical procedures in the abdominal cavity of the body generally require insufflating gases to raise the cavity wall away from vital organs, the procedure is usually initiated by use of a Verres needle through which a gas is introduced into the body cavity. The gas provides a slight pressure which raises the wall surface of the peritoneum away from the vital organs thereby providing an adequate region in which to operate. Thereafter, a trocar assembly which includes a cannula and a trocar or obturator is inserted within the cannula to puncture the peritoneum, i.e. the inner lining of the abdominal cavity wall. The obturator is removed and laparoscopic or endoscopic surgical instruments may then be inserted through the cannula to perform surgery within the abdominal cavity. The cannula may also be utilized for introducing tubes into the body as for drainage purposes, for specimen removal, for diagnostic evaluations, or the like.

In view of the need to maintain the atmospheric integrity of the inner area of the cavity, a valve assembly for a cannula which permits introduction of an obturator and a wide range of surgical instruments and which maintains the atmospheric integrity of the inner area of the cavity is desirable.

Generally, in the context of insufflatory, minimally invasive surgical procedures, cannula assemblies include structure(s) that two sealing requirements. The first requirement is to provide a substantially fluid tight seal when an instrument is not present in the cannula. The second requirement is to provide a substantially fluid tight seal when an instrument is being introduced into or already is present in the cannula. In this regard, there have been a number of attempts in the prior art to provide such sealing requirements.

U.S. Pat. No. 4,655,752 to Honkanen et al. teaches a cannula including a housing and first and second seal members. The first seal member is conically tapered toward the bottom of the housing and has a circular opening in its center, while the second seal is conically tapered and cup shaped. The second seal includes at least one slit to allow for the passage of instruments.

U.S. Pat. No. 4,929,235 to Merry et al. teaches a self-sealing catheter introducer having a sealing mechanism to prevent blood or fluid leakage. The sealing mechanism includes a planar sealing element having a slit and a conical sealing element. The sealing elements are each adapted to surround a tube.

U.S. Pat. Nos. 4,874,377 and 5,064,416 to Newgard et al. relate to a self-occluding intravascular cannula assembly in which an elastomeric valving member is positioned transversely to a housing and is peripherally compressed to cause displacement, distortion and/or rheological flow of the elastomeric material. A frustoconical dilator projection cooperates with the elastomeric valving member in moving the valving member to a non-occluding position.

U.S. Pat. No. 5,300,033 to Miller suggests a valve construction including an elastic body having a cylindrical wall with first and second walls formed integrally with the cylindrical wall. The second wall includes a slit to permit passage of a surgical instrument and first and second leaflets which define the slit. The leaflets are thicker in cross section to provide an additional closing force at the slit.

Cannula assemblies have also been developed with a series of resilient sealing elements having a central aperture, e.g., commonly assigned application Ser. Nos. 07/874,291, filed Apr. 24,1992 and 07/873,416, filed Apr. 24, 1992. Upon insertion of an instrument, the sealing elements resiliently receive and form a seal about the instrument. Upon withdrawal of the instrument, a fluid tight seal is provided by the internal sealing elements.

A disadvantage of several known valve systems for cannulas concerns the difficulty encountered in inserting and advancing the surgical instrument through the valve unit. In particular, since known elastomeric seal members are designed to form and maintain a fluid tight seal about the instrument, the aperture or slit within the seal through which the instrument is passed is of relatively small or narrow dimension. Further, portions of the valve member defining the aperture are generally thick in cross-section to provide a sufficient closing force of the seal about the instrument, see, e.g., U.S. Pat. No. 5,300,033. As a consequence of these design considerations, the level of force needed to insert and advance the instrument through the seal aperture is increased, thereby requiring awkward maneuvering on the surgeon's behalf to appropriately position the instrument for the desired surgery. Moreover, known valve systems are generally ineffectual in accommodating instruments of differing diameter while maintaining acceptable insertion forces and facilitating the range of desired surgical manipulations, e.g., angular instrument movements and specimen removal.

Accordingly, the present invention obviates the disadvantages of the prior art by providing a valve unit or assembly for a cannula assembly, which is capable of forming and maintaining a tight seal about instruments of varying diameters inserted through the cannula and which incorporates structure to enhance and facilitate passage of the instrument through the valve unit.

SUMMARY

Generally stated, the present disclosure is directed to a valve assembly for sealed reception of an elongated object. The assembly includes a valve body having at least one opening configured and dimensioned to permit entry of an elongated object and defining a central longitudinal axis, an elongated seal member formed of a resilient material and defining an aperture in general alignment with the opening of the valve body whereby the aperture is configured and dimensioned such that insertion of the object into the aperture causes the resilient material defining the aperture to resiliently engage the outer surface of the object in a substantially fluid tight manner, and at least one elongated guard member disposed within the valve member in supporting contact with the inner surface thereof and positioned to engage the elongated object upon at least partial insertion of the elongated object into the valve body. The guard member includes at least a first substantially rigid portion adapted to be displaced relative to the longitudinal axis to facilitate expansion of the aperture of the seal member and a second portion having less rigidity than the first portion of the guard member to enhance passage of the elongated object through the valve body. The second portion of the guard member may be positioned adjacent the aperture of the seal member to provide an interface between the guard member and the seal member to thereby protect the portions of the seal member defining the aperture from engagement with the elongated object.

The preferred guard member is a monolithically formed single piece unit wherein the first portion of the guard member defines a cross-sectional dimension which is greater than the cross-sectional dimension of the second portion, thus providing the more rigid characteristic to the first portion.

In a preferred embodiment, the valve assembly includes a valve housing having a longitudinal opening configured and dimensioned to permit entry of an elongated object, an elongated resilient seal member at least partially positionable within the valve housing and defining an aperture to permit entry of the elongated object therein in a substantially fluid tight manner and a plurality of guard members disposed within the seal member and concentrically arranged about a central longitudinal axis defined by the valve housing. The plurality of guard members are positioned to engage the elongated object upon insertion of the elongated object within the valve housing and are adapted to be radially displaced upon introduction of the elongated object to engage portions of the seal member defining the aperture to expand the aperture. Each guard member possesses an end portion of less rigidity than the remaining portion(s) of the guard member wherein the end portion of less rigidity reduces the force required to advance the elongated object through the valve housing.

The guard members of this embodiment are preferably pivotally mounted to a generally annular guard mount and extend generally longitudinally within the seal member. The end portions of the guard members overlap to form an iris-like arrangement. Upon entry of the elongated object, the guard members simultaneously pivot outwardly to uniformly engage and stretch or dilate the inner surfaces of the seal member to open or expand the aperture.

The elongated seal member of the valve assembly preferably includes a central frusto-conical portion which accommodates the guard members and a circumferential portion. The circumferential portion includes a bellows structure which is engageable with the valve housing and dimensioned to maintain a substantially fluid tight seal with the valve housing upon manipulation of the elongated object within the aperture. In particular, the bellows structure enables the seal member to float within the valve housing while maintaining a fluid tight seal about the elongated object and within the housing.

The valve assembly is intended to be used in combination with a cannula including a cannula housing and a cannula sleeve extending distally from the cannula housing and is preferably detachably connectable to the cannula housing. The cannula housing may include a valve member disposed therein which is moveable between a substantially closed position in the absence of an instrument to an open position in the presence of an instrument.

BRIEF DESCRIPTION OF THE DRAWINGS

Various embodiments are described hereinbelow with reference to the drawings wherein.

DETAILED DESCRIPTION OF PREFERRED EMBODIMENT(S)

The present disclosure contemplates the introduction into a person's body of all types of surgical instruments including clip appliers, graspers, dissectors, retractors, staplers, laser fibers, photographic devices, endoscopes and laparoscopes, tubes, and the like. All such objects are referred to herein as "instruments".

Figure 1:
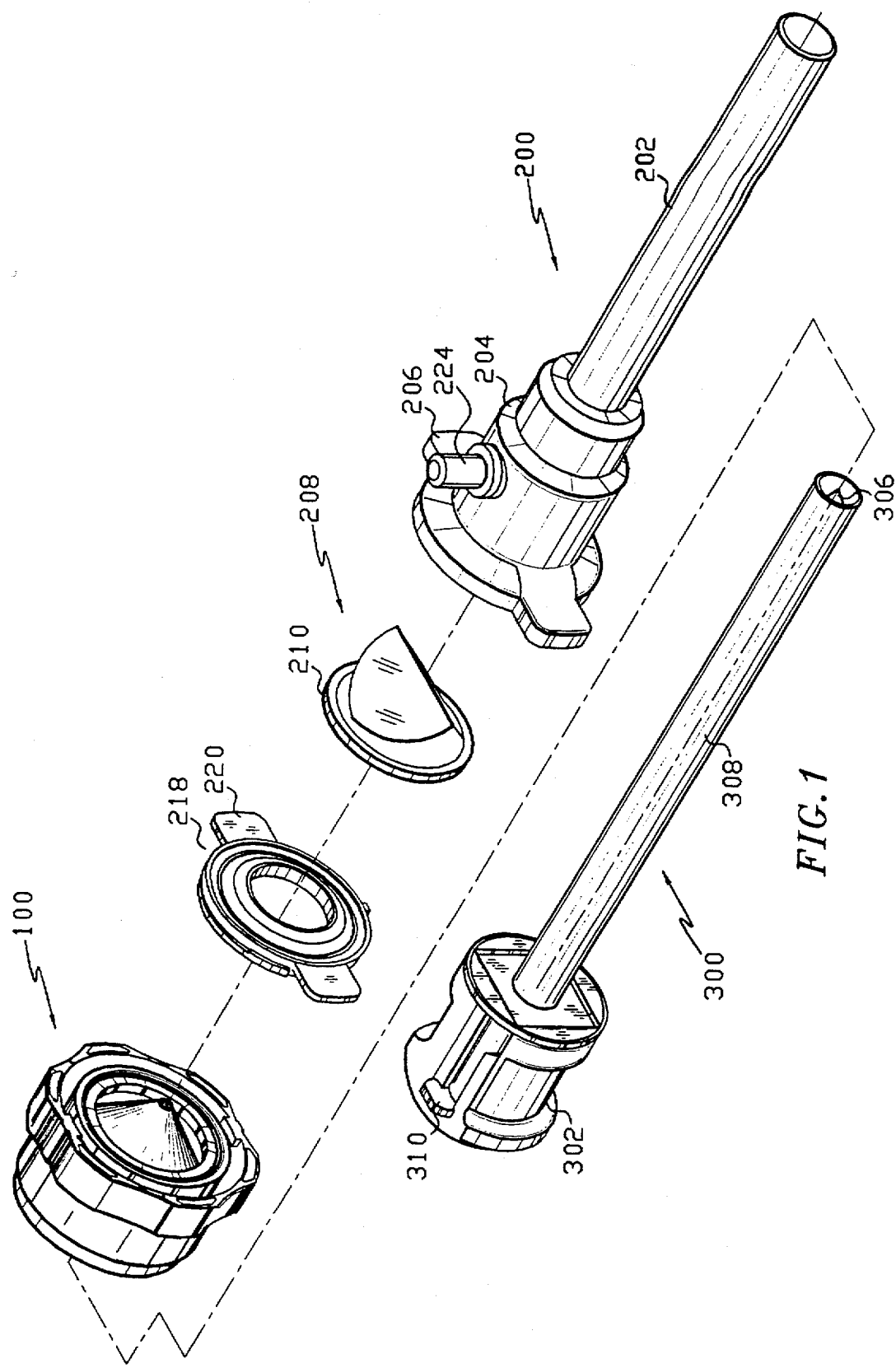
FIG. 1 is a perspective view with parts separated of a trocar assembly cannula assembly and valve assembly constructed according to the principles of the present disclosure.

Referring initially to FIG. 1, there is illustrated the novel valve assembly 100 constructed in accordance with the principles of the present disclosure and intended to be used in combination with a conventional trocar assembly consisting of cannula assembly 200 and trocar 300.

The valve assembly of the present disclosure, either alone or in combination with a valve unit/seal assembly internal to cannula assembly 200, and either integral with or detachably mounted to cannula assembly 200, provides a substantial seal between a body cavity of a patient and the outside atmosphere, both, during and subsequent to insertion of an instrument through the cannula. Moreover, the valve assembly 100 of the present disclosure is capable of accommodating instruments of varying diameter, e.g. from 5 mm to 12 mm, by providing a gas tight seal with each instrument when inserted. The flexibility of the present valve assembly greatly facilitates endoscopic surgery where a variety of instruments having differing diameters are often needed during a single surgical procedure.

The valve assembly is preferably detachably mountable to the proximal end of cannula assembly 200 disclosed herein. Thus, the surgeon can remove the valve assembly 100 from the cannula assembly 200 at any time during the surgical procedure and, similarly, mount the assembly 100 to the cannula when desired to provide a sealing engagement with an instrument to be inserted through the cannula assembly. In addition, the valve assembly 100 may be readily adapted to be mounted to conventional cannulas assemblies of differing structures. The detachability of valve assembly 100 from cannula assembly 200 facilitates specimen removal through cannula assembly 200 and reduces the profile of cannula assembly 200 when valve assembly is not needed for the surgical procedure.

Figure 2:
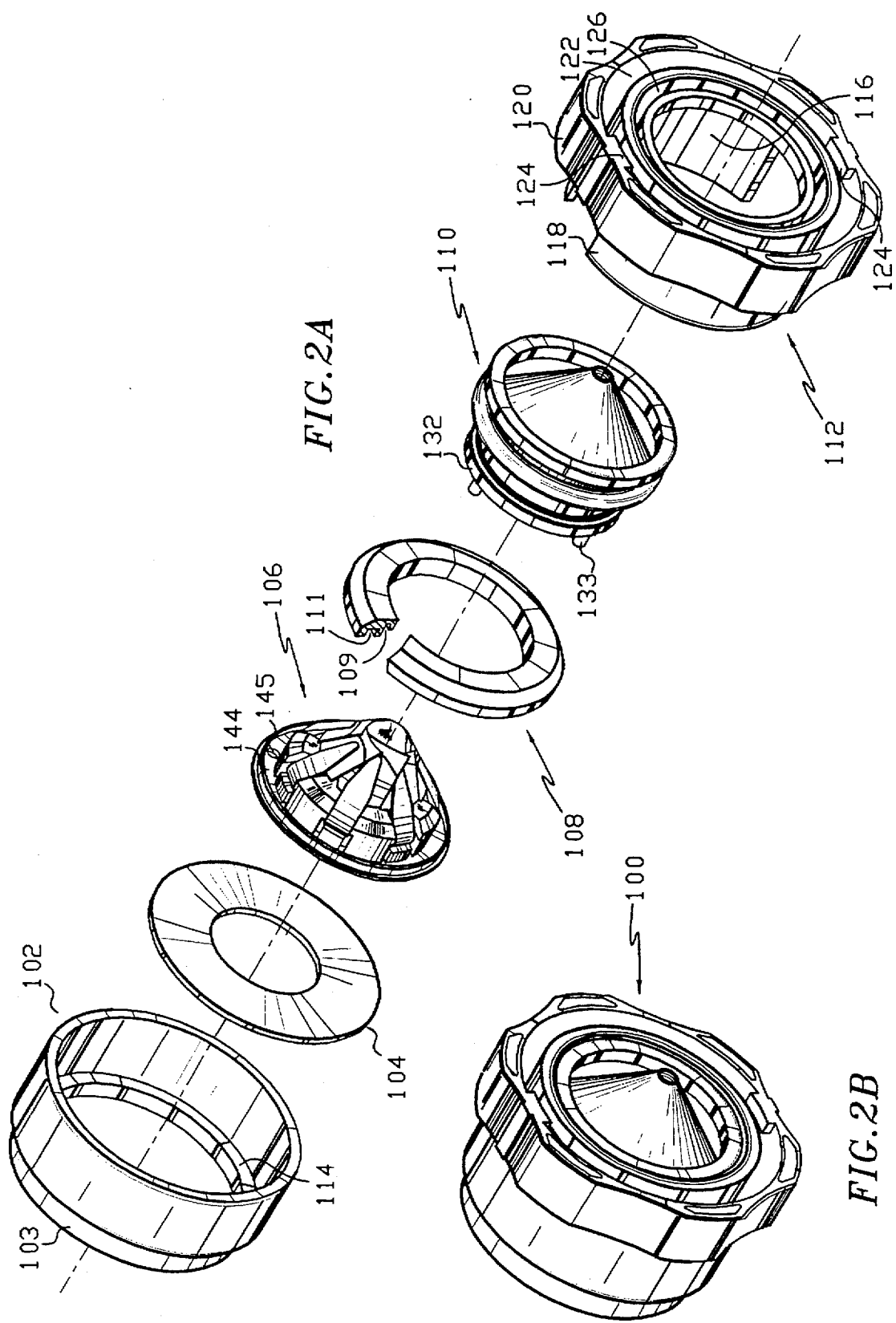
FIG. 2A is an exploded perspective view with parts separated of the valve assembly of FIG. 1.
FIG. 2B is a perspective view of the valve assembly in the assembled condition.

Referring now to FIGS. 2A and 2B, the novel valve assembly of the present disclosure will be discussed in detail. As shown in the exploded view of FIG. 2A, Valve assembly 100 includes end cap 102, stabilizer plate 104, guard mount 106, guard holder 108, seal element 110 and seal housing 112. End cap 102, stabilizer plate 104 and seal housing 112 form the outer valve body of the assembly, which houses the sealing and dilating components of the system, i.e., guard mount 106, guard holder 108 and seal element 110.

End cap 102 is generally cylindrically-shaped and includes a proximal end portion 103 defining a diameter which is less than the diameter of the remaining portion of the end cap and an inner peripheral ledge 114 which supports stabilizer plate 104. Guard holder 108 is ring-like in configuration and includes inner and outer peripheral grooves 109, 111 respectively formed in its proximal face. Grooves 109, 111 assist in retaining guard mount 106 within seal 110. Seal housing 112 includes central opening 116, a proximal cylindrical portion 118 and a distal outer flange 120 having a scalloped surface to facilitate handling thereof. Cylindrical portion 118 is received within end cap 102 when the valve assembly is fully assembled to enclose the sealing components. The distal end face of seal housing 112 includes a peripheral groove 122 and two opposed rib portions 124 extending radially inwardly adjacent the groove 122. Groove 122 and rib portions 124 assist in mounting valve assembly 100 to cannula assembly 200 as will be appreciated from the description provided below. The distal end face of seal housing 112 also includes a second groove 126 adjacent opening 116 for accommodating a portion of seal 110.

Figure 3:
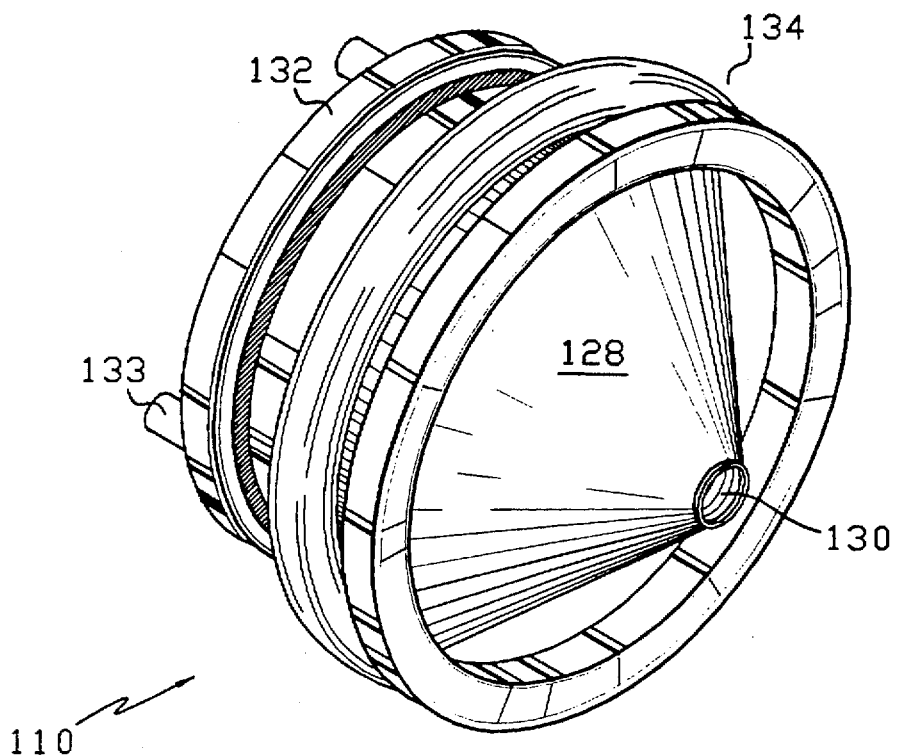
FIG. 3 is an enlarged perspective view of the resilient seal member of the valve assembly of FIG. 2A.
Figure 4:
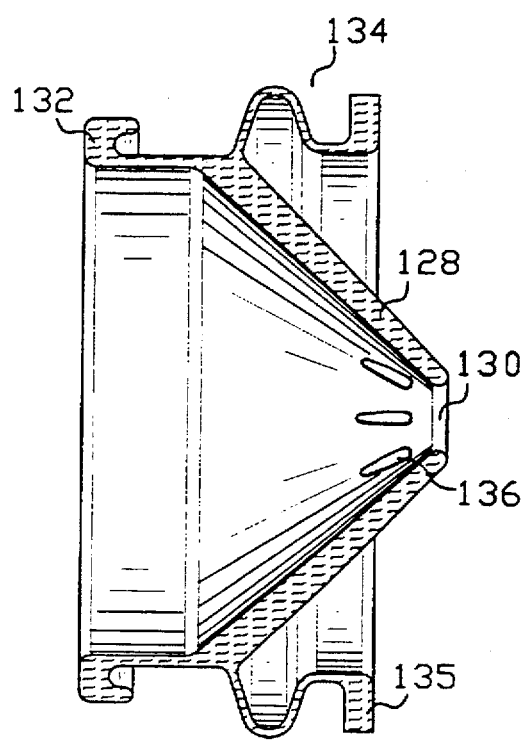
FIG. 4 is a cross-sectional view of the seal member of FIG. 3.

Referring now to FIGS. 2A, 3 and 4, sealing element 110 includes a generally frusto-conical interior portion 128 defining aperture 130, a circumferential flange portion 132 at its proximal end and circumferential bellows structure 134 disposed adjacent the distal end of the seal 110 and having distal outer flange portion 135. Seal 110 is fabricated from an elastomeric material such as synthetic or natural rubber which is preferably sufficiently resilient to accommodate and provide a fluid seal with instruments of varying diameters inserted through aperture 130, e.g., instruments ranging in diameter from about 5 mm to about 12 mm, and sufficiently resilient to flex at bellows structure 134 to accommodate manipulation of instrumentation inserted through aperture 130. A plurality of generally longitudinally extending ribs 136 are disposed along the inner surface of frusto-conical portion 128. Ribs 136 provide additional support to seal 110 and are intended to engage the elongated instrument upon insertion thereof through the seal to minimize the potential of damage such as cutting or tearing of the seal by the distal end of the instrument. Flanges 132, 135 function in mounting seal 110 to the valve body as will be appreciated from the following description. Seal 110 may also include at least one aligning projection 133 extending from its proximal face to assist in mounting the seal to guard mount 106. Preferably seal 110 includes three projections 133.

Figure 5:
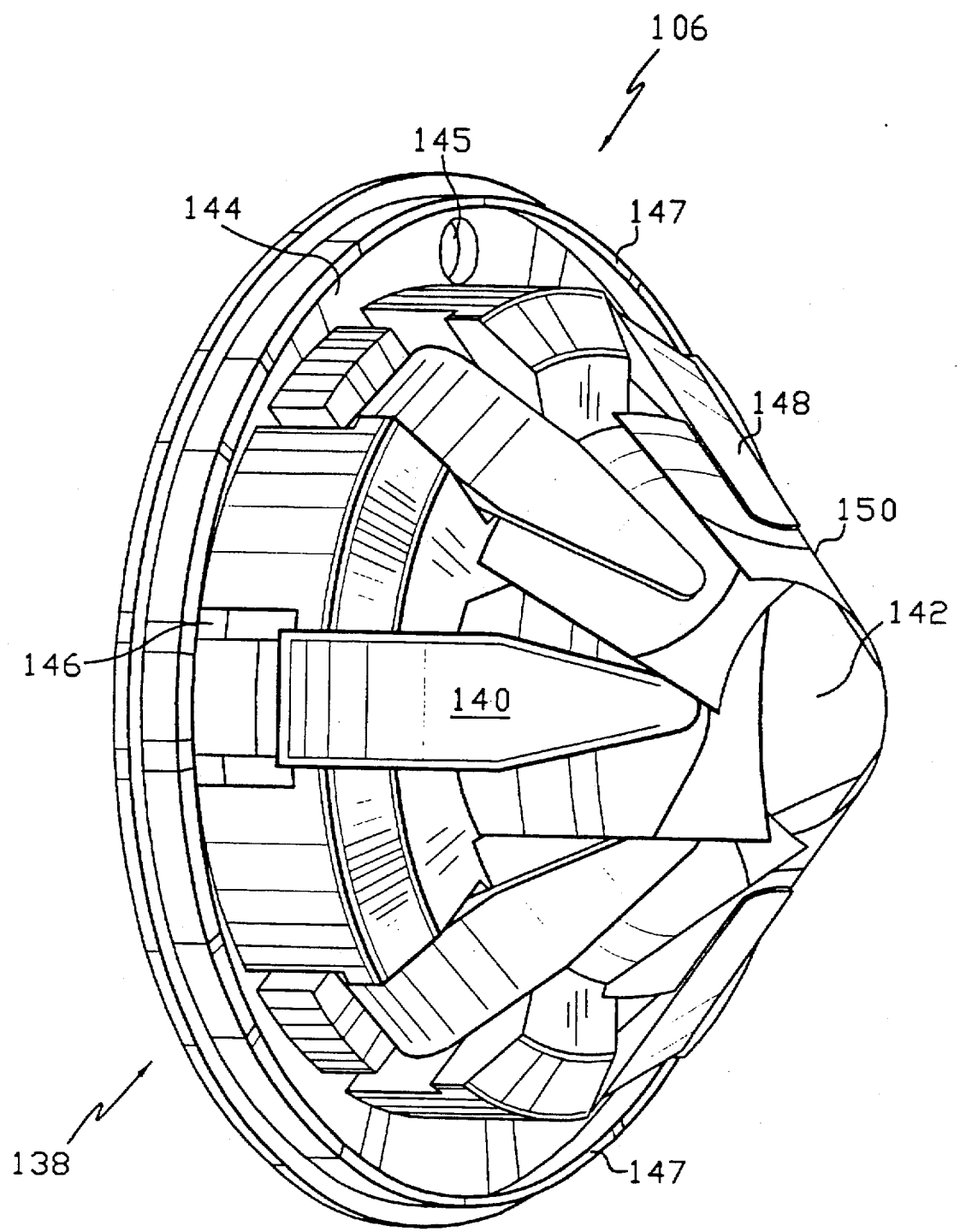
FIG. 5 is an enlarged perspective view of the guard mount of the valve assembly of FIG. 2A illustrating the guard members supported by the guard mount.
Figure 6:
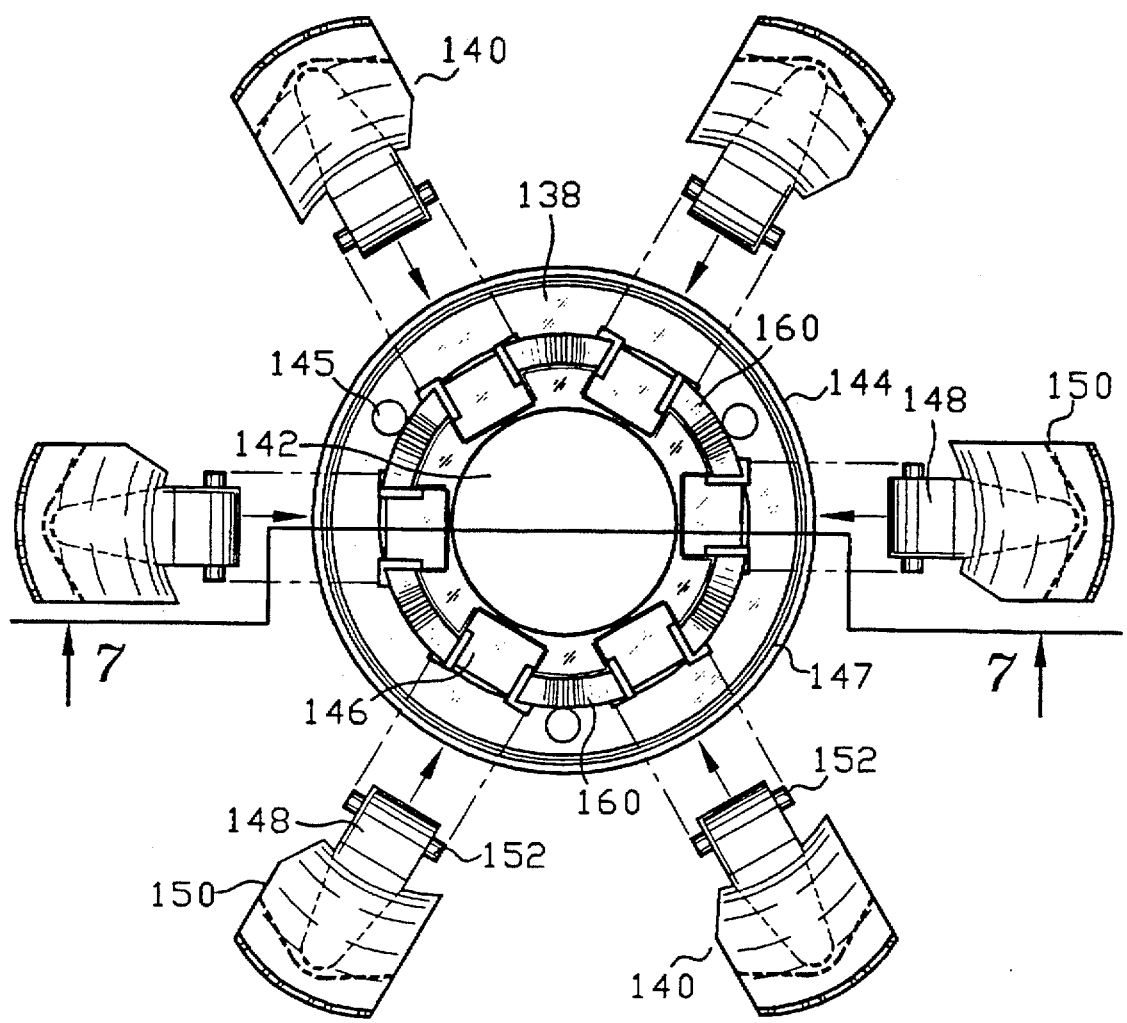
FIG. 6 is a top plan view of the guard mount of FIG. 5 with the guard elements disassembled from the guard mount.
Figure 7:
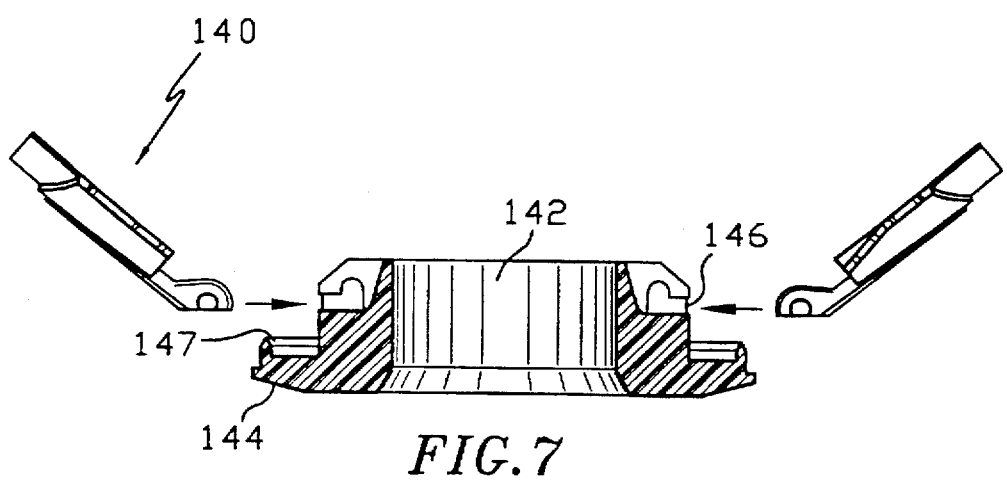
FIG. 7 is a cross-sectional view taken along the lines 7—7 of FIG. 6.

Referring now to FIG. 2A, in conjunction with FIGS. 5-7, guard mount 106 of valve assembly 100 will be discussed. Guard mount 106 includes an annular base portion 138 and a plurality of guard elements 140 pivotally mounted relative to the base portion. Base portion 138 defines a central opening 142 which is variably dimensioned to permit passage of an instrument therethrough, as discussed below, and an outer circumferential flange 144 at its proximal end. Circumferential flange 144 includes a circumferential lip 147 and three apertures 145 correspondingly dimensioned to accommodate the three aligning projections 133 extending from seal 110 (FIG. 2A).

Guard mount 106 also includes a plurality of slots 146 (FIG. 6) defined in the outer wall of base portion 138 for accommodating the proximal ends of guard elements 140. Slots 146 are equidistantly disposed about base portion 138 and extend generally longitudinally from a position intermediate the proximal and distal ends of the guard mount 106 through the distal end face of the base portion 138.

Each guard element 140 includes a finger-like portion 148 and an outer flap portion 150 connected at distal end of finger portion 148. Flap portion 150 may be joined to finger portion 148 in a variety of manners, e.g., adhesive or insert molding, or flap portion 150 and finger portion 148 may preferably be an integrally molded component. Finger portions 148 are accommodated within respective slots 146 in guard mount 106 and include a pair of opposed projecting members 152 extending outwardly from their proximal ends (FIG. 6). Projecting members 152 serve in pivotally mounting guard elements 140 to guard mount 106.

As best shown in FIGS. 7 and 8A–8C, the outer flap 150 of each guard element 140 defines first and second portions 154, 156 of varying thicknesses. The first or proximal portion 154 has a cross-sectional dimension or thickness which is greater than the thickness of the second or distal portion 156 of the outer flap 150. Preferably, first portion 154 is from about two to about three times thicker in cross-sectional dimension than second portion 156. This dimensional ratio translates to second portion 156 being about two to three times more flexible than first portion 154, assuming the same material of construction. Such dimensioning of outer flap 150 ensures that guard elements 140 are sufficiently rigid to cause stretching surface of the seal surface portions 110 defining seal aperture 130 to thereby increase the dimension of the aperture 130 and facilitate insertion of the instrument therethrough and, in addition, provide sufficient flexibility to minimize the force required to advance the instrument through the guard element and seal arrangement.

More specifically, by the strategic dimensioning of the guard elements 140 the following characteristics are present: 1) the finger portion 148 in combination with the relative thick first portion 154 of outer flap 150 provides a substantially rigid section of the guard element 140, which section is capable of sufficiently engaging the inner frustoconical surface 128 of seal 110 and enlarging the aperture 130 of the seal by displacing seal portions defining the aperture 130 radially outwardly; and 2) the relatively thin and less rigid, second portion 156 of outer flap 150 reduces the force required to pass the instrument through the guard mount and seal arrangement and, also, minimizes the risk of damage to the inner surface of the seal by providing a protective interface between the instrument and the inner wall. Inasmuch as guard elements 140 are pivotally mounted to guard mount 106, as an instrument contacts outer flap 150 along its length, i.e., both along first portion 154 and second portion 156, outer flap 150 is pivoted relative to projecting members 152 against seal 110 in dilating contact therewith.

Guard elements are fabricated from a suitable material such as high density polyethylene, and, as noted above, are preferably monolithically formed by injection molding techniques to define a single element. It is also possible for the finger portion 148 and flap portion 150 of guard element 140 to be individually formed and subsequently connected by adhesives or the like.

Figure 8A:
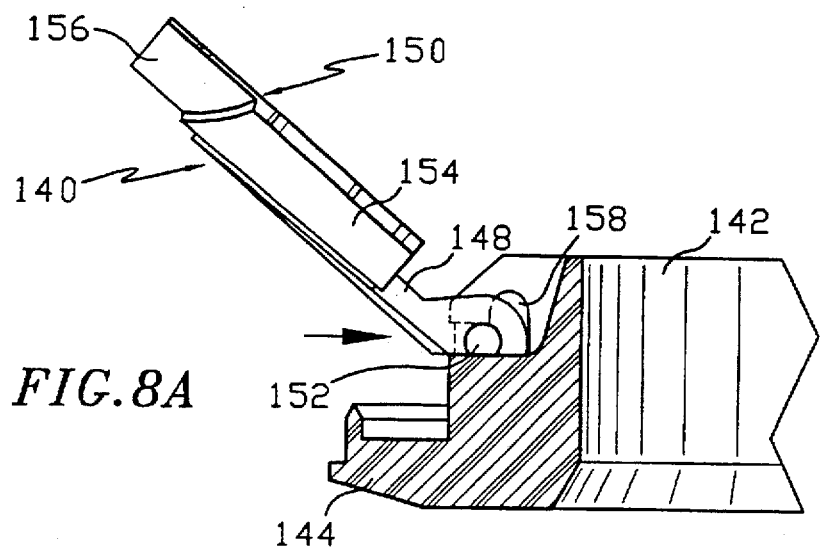
FIGS. 8A–8C are cross-sectional views of a portion of a single guard mount illustrating a preferred method for pivotally connecting a guard element to the guard mount.
Figure 8B:
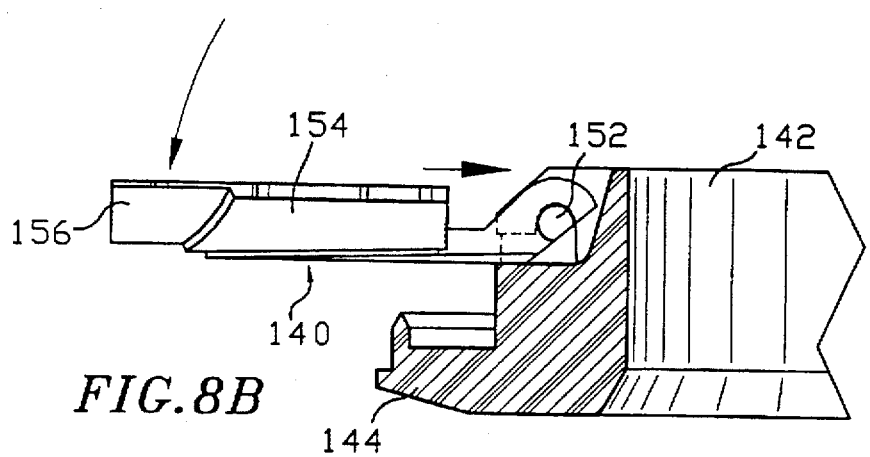
Figure 8C:
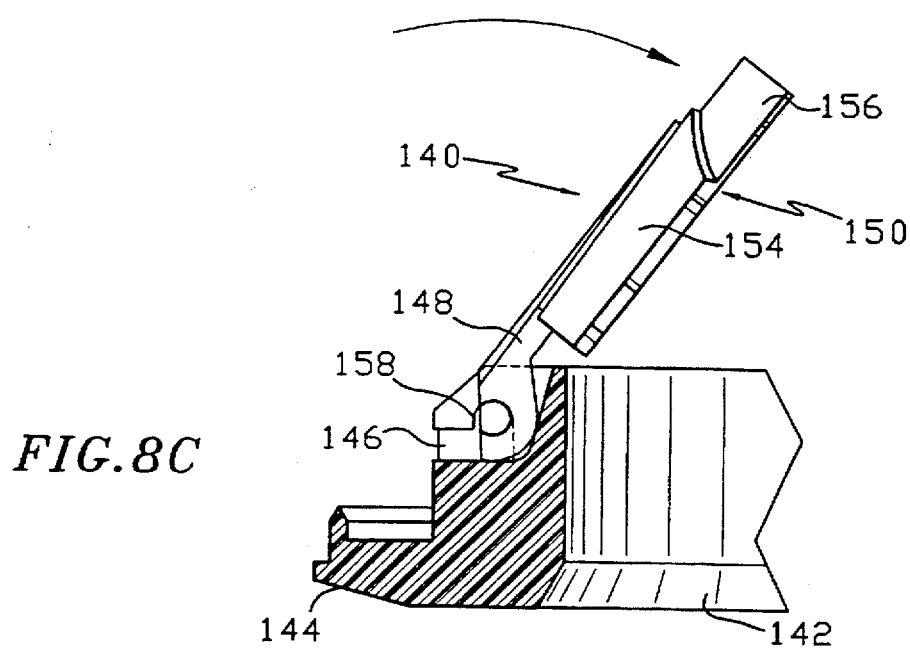

Referring now to FIGS. 6, 7, and 8A–8C, the mounting of each guard element 140 to guard mount 106 will be discussed in detail. Each guard element 140 is individually mounted within a slot 146 in base portion 138 of guard mount 106 by inserting the proximal finger portion 148 within the base of the slot as shown in FIG. 8A and advancing the guard element into the slot such that the opposed projecting members 152 snap into correspondingly dimensioned grooves 158 (FIGS. 8A–8C) formed in portions 160 of base 138 adjacent each slot.(see FIG. 6) FIG. 8B depicts the projecting members 152 locked into grooves 158. Thereafter, each guard element 140 is pivoted upwardly to its appropriate position as shown in FIG. 8C.

Figure 9:
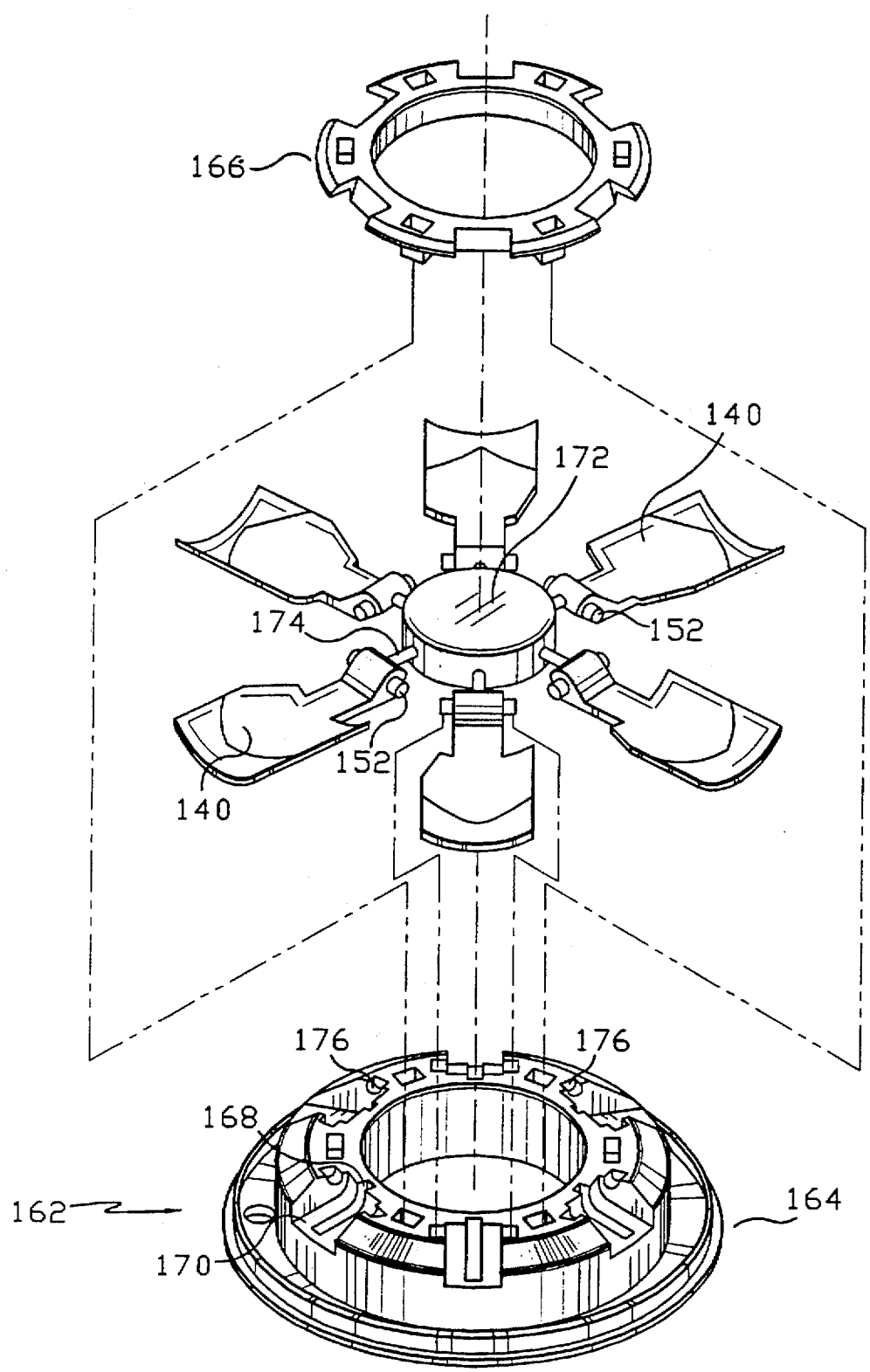
FIG. 9 is an alternative two-piece guard mount to be incorporated in the valve assembly of FIG. 2A and illustrates a preferred method for mounting the guard elements to the guard mount.

FIG. 9 illustrates an alternative guard mount 162, and assembly method therefor, to be incorporated in the valve assembly 100 of the present disclosure. In accordance with this embodiment, guard mount 162 includes lower half section 164 and upper half section 166 positionable on the lower half section. Guard mount 162 is substantially identical in configuration to the guard mount 106 described in connection with FIGS. 5–7 except that this guard mount 162 is provided with a radial groove 168 which is disposed adjacent each slot 170. In further accordance with this embodiment, the guard elements 140 are simultaneously integrally molded to define a single unit as shown in FIG. 9. In the single molded unit, each guard element 140 is appropriately positioned and oriented to be placed within a corresponding slot 170 within the lower half section 164 of guard mount 162, i.e., during assembly, the single unit is positioned against the lower section 164 with guard elements 140 being received within the slot portions 170. Thereafter, the central molded portion 172 and the stems 174 interconnecting the guard elements 140 and the central molded portion are removed leaving the guard elements 140 within their respective slots. It is to be appreciated that a portion of stem 174 connected to each guard element 140 may remain after removal of the central portion 172. This stem portion is received within radial groove 168 in assembly and serves to resist any tendency of the guard element 140 to rotate out of its respective slot 170. Once the guard elements 140 are positioned within their respective slots 170 with the opposed projections 152 in place within grooves 176 in guard mount 162, the upper section 166 of the guard mount is attached to the lower section by adhesives, spot welding or the like. The assembled guard mount 160 and guard elements 140 operate in a similar manner to that described in connection with mount 106 of FIG. 5.

Referring again to FIG. 5, the guard elements 140 in their fully assembled position may be oriented define a generally frusto-conical configuration so as to be positioned within the frusto-conical portion 128 of seal 110. Preferably, guard elements 140 are arranged in overlapping relation, i.e., whereby outer flap portions 150 of adjacent guard elements 140 overlap each other to define a general iris-like arrangement of the guard elements. This desired arrangement is achieved by pivoting a first guard element 140 inwardly and thereafter sequentially pivoting the remaining guard elements onto each other. Once all the guard elements 140 are in a fully pivoted position, the leading edge of the outer flap portion 150 of the last pivoted guard element 140 is tucked under the trailing edge of the flap portion 150 of the first pivoted guard element to provide the arrangement shown in FIG. 5.

Referring now to FIGS. 2A–2B, in conjunction with FIGS. 10–11, the assembling of the components of valve assembly 100 will be discussed in detail. Although in FIGS. 10 and 11 the valve assembly 100 is shown already mounted to cannula assembly 200, it is to be appreciated that generally valve assembly 100 is first assembled as a single unit and then mounted to the cannula assembly. The mounting of valve assembly 100 to cannula assembly 200 will be discussed below. Stabilizer plate 104 is positioned within end cap 102 such that the plate 104 rests on inner peripheral ledge 114 defined within the end cap 102. Thereafter, guard holder 108 is positioned over the proximal flange 132 (FIG. 4) of seal 110 whereby the inner peripheral groove 109 of the guard holder 108 receives and accommodates the proximal flange 132 of the seal 110. Thereafter, seal 110 and guard holder 108 are positioned over guard mount 106 (FIG. 5) and advanced onto the mount until proximal flange 132 of the seal is abutting circumferential flange 144 of the mount 106 and aligning projections 133 are received within apertures 145 (FIG. 2A and FIG. 5) formed in the circumferential flange 144 as shown in cross-section in FIG. 11. In this position, the circumferential lip 147 on circumferential flange 144 (FIG. 5) is received within the outer groove 111 of guard holder 108.

Assembly is continued by placing the assembled seal 110, guard holder 108 and guard mount 106 subassembly against stabilizer plate 104 which is positioned against ledge 114 within end cap 102. Thereafter, seal housing 112 is positioned over the entire unit with the cylindrical wall 118 of the seal housing being received within the cylindrical wall of end cap 102. In this assembled condition, the distal end portion of the cylindrical wall of end cap 102 is received within an annular space defined between distal flange 120 of seal housing 112 and cylindrical wall 118 of seal housing 112 and retained therein by a friction or snap fit, thus retaining the valve assembly in a fully assembled condition. It is to be noted that in the assembled condition the distal flange 135 of bellows structure 134 of seal 110 is a positioned over the distal face of seal housing 112 wherein the flange 135 is received within second circumferential groove 126 of the seal housing.

The valve assembly 100 now in its fully assembled condition can be mounted to cannula assembly 200. Referring to FIGS. 1, 10 and 11, cannula assembly 200 is part of a trocar assembly and includes a cannula sleeve 202 and a cannula housing 204 mounted on one end of the sleeve. Sleeve 202 defines a cannula passage in its interior and may be formed of stainless steel or other rigid materials such as polymeric materials or the like.

Cannula housing 204 is rigidly secured to the proximal end of cannula 202 and defines a longitudinal opening for reception and passage of an elongated surgical instrument. The proximal end portion of the cannula housing 204 defines a generally circular cross-section and possesses diametrically opposed leg portions 206. A cannula seal 208 fabricated from a resilient material, e.g., rubber, is positioned within the interior of cannula housing 204. Seal 208 includes a circumferential flange portion 210 which rests on a correspondingly dimensioned circumferential ledge 212 within cannula housing 204. Seal 208 generally defines a duck bill shape having two planar tapering portions 214 which intersect at their distal ends to define abutment face 216. The planar tapering portions 214 may each include one or more inwardly directed, longitudinally oriented ribs to facilitate instrument passage. Abutment face 216 permits passage of the elongated object through the seal 208, but in the absence of an instrument, and particularly when cannula 202 is inserted into an insufflated body cavity, abutment face 216 forms a gas-tight seal that isolates the insufflated cavity from the ambient surroundings. Seal 208 also includes at least one, preferably two, reinforcing ribs 215 to stabilize the seal. Ribs 215 are positioned to engage the instrument to guide the instrument through slits 216 and prevent piercing of the seal 208 by the tip of the instrument.

Cannula assembly 200 also includes a stabilizing plate 218 (FIG. 1) which is positioned against the flange portion 210 of seal 208 to provide support for the seal during introduction and withdrawal of an elongated instrument. Stabilizing plate 218 includes two diametrically opposed extensions 220 (FIG. 1) which are received within the correspondingly dimensioned leg portions 206 of the cannula housing 204. In the preferred embodiment, stabilizing plate 218 is securely attached to cannula housing 204 at contact points along the extensions of the respective components by spot welding, adhesives or the like. Stabilizing plate 218 also includes a partial external annular rib or thread 222 (FIG. 11) adjacent its proximal end, the function of which will be appreciated from the description below.

A stop cock valve 224 may be incorporated as part of cannula housing 204 to permit the passage of insufflation gases through the cannula and into the body cavity. A suitable valve for this purpose is available from the Burron OEM Division of B. Braun Medical, Inc. (Model No. 55401022).

Figure 10:
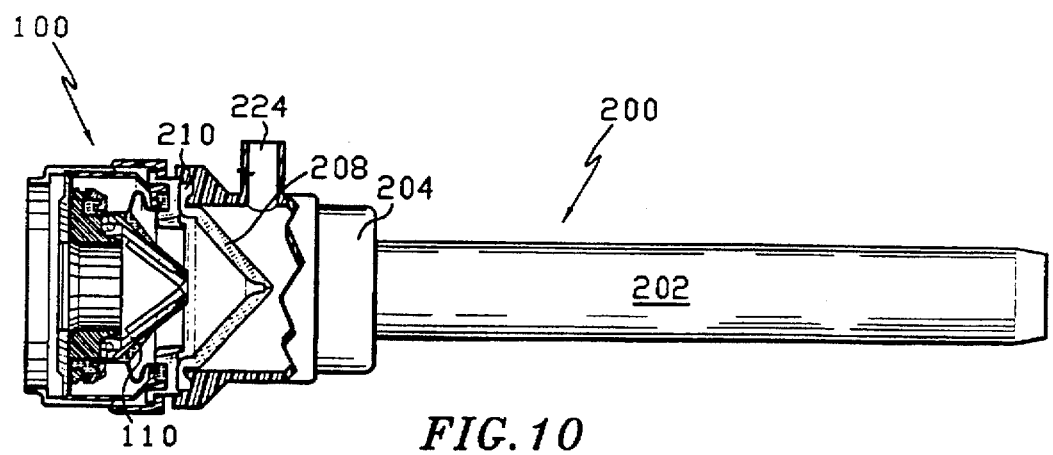
FIG. 10 is a side plan view in partial cross-section of the cannula housing and the valve assembly detachably mounted the cannula housing of the cannula assembly.
Figure 11:
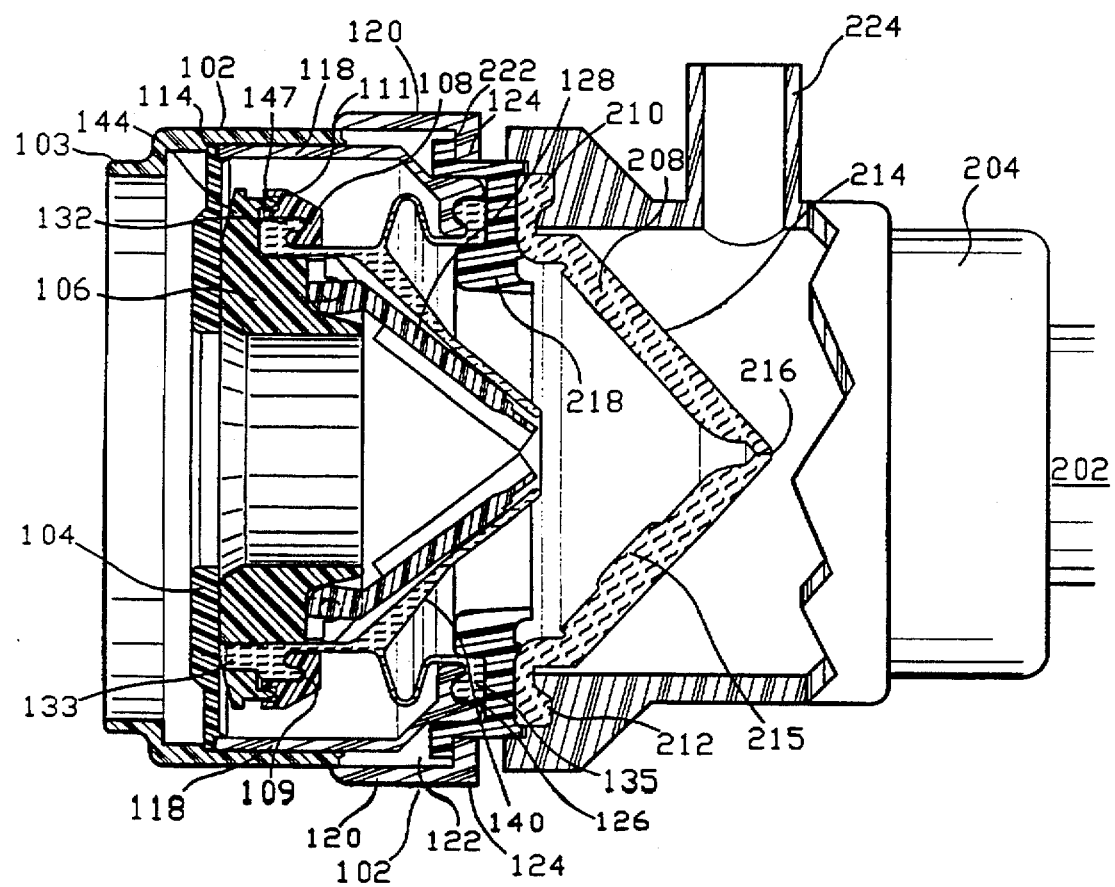
FIG. 11 is an enlarged cross-sectional view illustrating the valve assembly and the cannula housing.

Referring still to FIGS. 1, 10 and 11, the mounting of valve assembly 100 to cannula housing 204 will be discussed. The assembled valve assembly 100 is detachably mounted adjacent stabilizing plate 218 with the partial annular thread 222 of the stabilizing plate 218 being received within the peripheral groove 122 (FIG. 2a) defined in the distal face of seal housing 112. The valve assembly 100 is rotated to cause engagement of the radially inwardly projecting rib portions 124 adjacent groove 122 with the partial annular thread 222 to releasably lock the valve assembly 100 to the cannula housing. Other means for detachably connecting the valve assembly 100 to cannula housing 204 can be readily determined by one skilled in the art such as screw threads, adhesives, bayonet locking, and the like.

Figure 12:
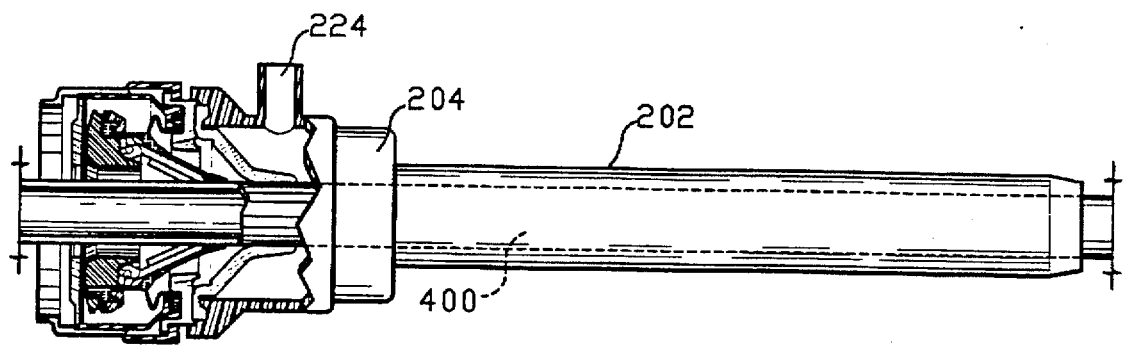
FIG. 12 is a view similar to FIG. 10 illustrating the introduction of an elongated object into the valve assembly and cannula assembly.
Figure 13:
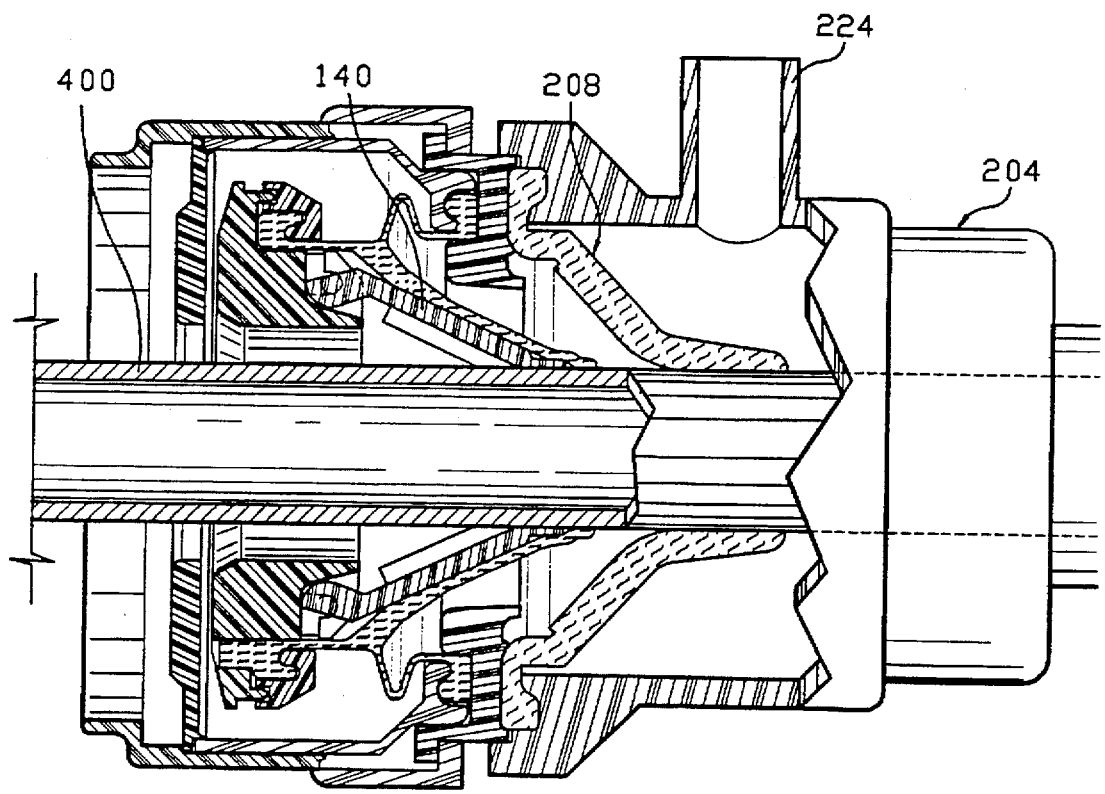
FIG. 13 is a view similar to FIG. 11 illustrating sealing engagement of the resilient seal member of the valve assembly with the elongated object.

Referring now to FIGS. 12 and 13, an elongated object such as a surgical instrument, identified generally as numeral 400, may be inserted through the valve assembly 100 and into the cannula 200 to perform the desired diagnostic procedure and/or surgery. As the surgical instrument enters the valve assembly, the tip of the surgical instrument is engaged by the guard elements 140. Upon further advancement of the surgical instrument, the guard elements 140 are pivoted radially outwardly to bias the seal member in an outward direction thereby stretching the seal portions defining the aperture 130 and increasing the dimension of the aperture to the degree necessary to accommodate instrument 400. As previously stated, the particular dimensioning of the guard elements 140, i.e. the rigid section in combination with the more flexible outer portion, ensures adequate stretching of the seal element 110 while also permitting relatively easy passage of instrument 400 through the valve assembly. In addition, the overlapping arrangement of the outer flap portions 150 of the guard elements facilitate dilation of the seal aperture and minimize the potential for the distal end of the instrument to contact and pierce the resilient material of the inner surface of seal 110 by providing an interface between the guard elements and the seal. The resilient seal member 110 sealingly engages to form a substantial fluid-tight seal about the surgical instrument and a fluid tight seal within the valve housing and the external atmosphere. The instrument 400 is advanced through the cannula assembly 200 whereby the duckbill seal of the cannula assembly also spreads to allow passage of the instrument. Once positioned within the valve assembly 100 and cannula assembly 200, the surgical instrument may be maneuvered about the internal body cavity.

Figure 14:
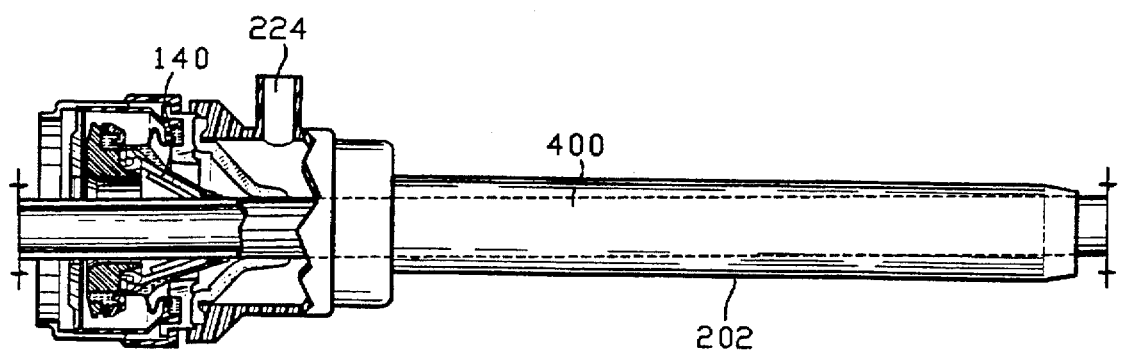
FIG. 14 is a view similar to FIG. 12 illustrating the adaptability of the valve assembly to radial movement of the elongated object in the cannula assembly.
Figure 15:
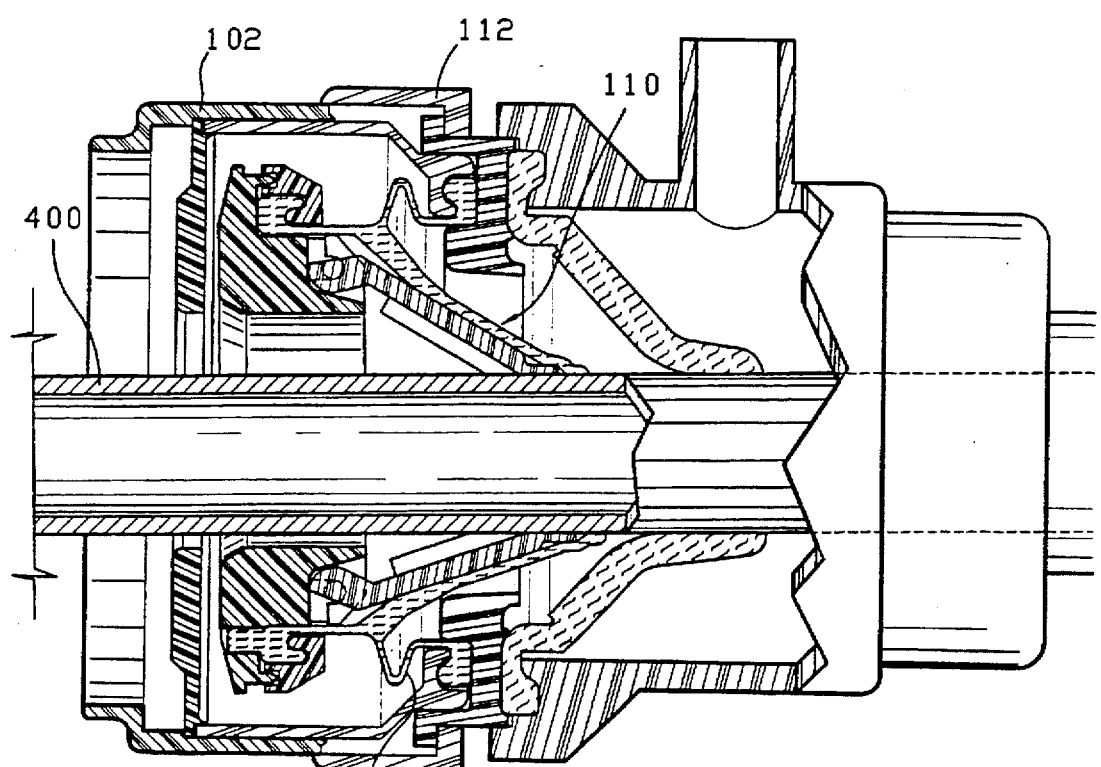
FIG. 15 is a view similar to FIG. 13 further depicting the adaptability of the valve assembly to accommodate for radial movement of the elongated member.

As shown in FIGS. 14–15, the valve assembly permits limited unencumbered movement of the instrument in a radial direction (relative to the centerline of sleeve 202) while still maintaining an adequate seal about the instrument. This is due to the strategic spacing of the inner valve components, i.e., guard mount 106 and seal 110, relative to the valve body, i.e., end cap 102 and seal housing 112, and the bellows structure 134 of the seal 110. In particular, the bellows structure 134 provides sufficient flexibility to permit the valve components to "float" within the valve housing while still preserving the integrity of the seals established about the surgical instrument and within the cannula assembly. Thus, manipulation of the instrument in any direction, either longitudinally or radially, to he extent permitted by the rigid housings and cannula, will not effect the seal, since the resilient material of the seal element and the bellows structure will conform to the movements of the instrument and assume a desired shape necessary to retain sealing contact with the instrument.

Figures 16, 17:
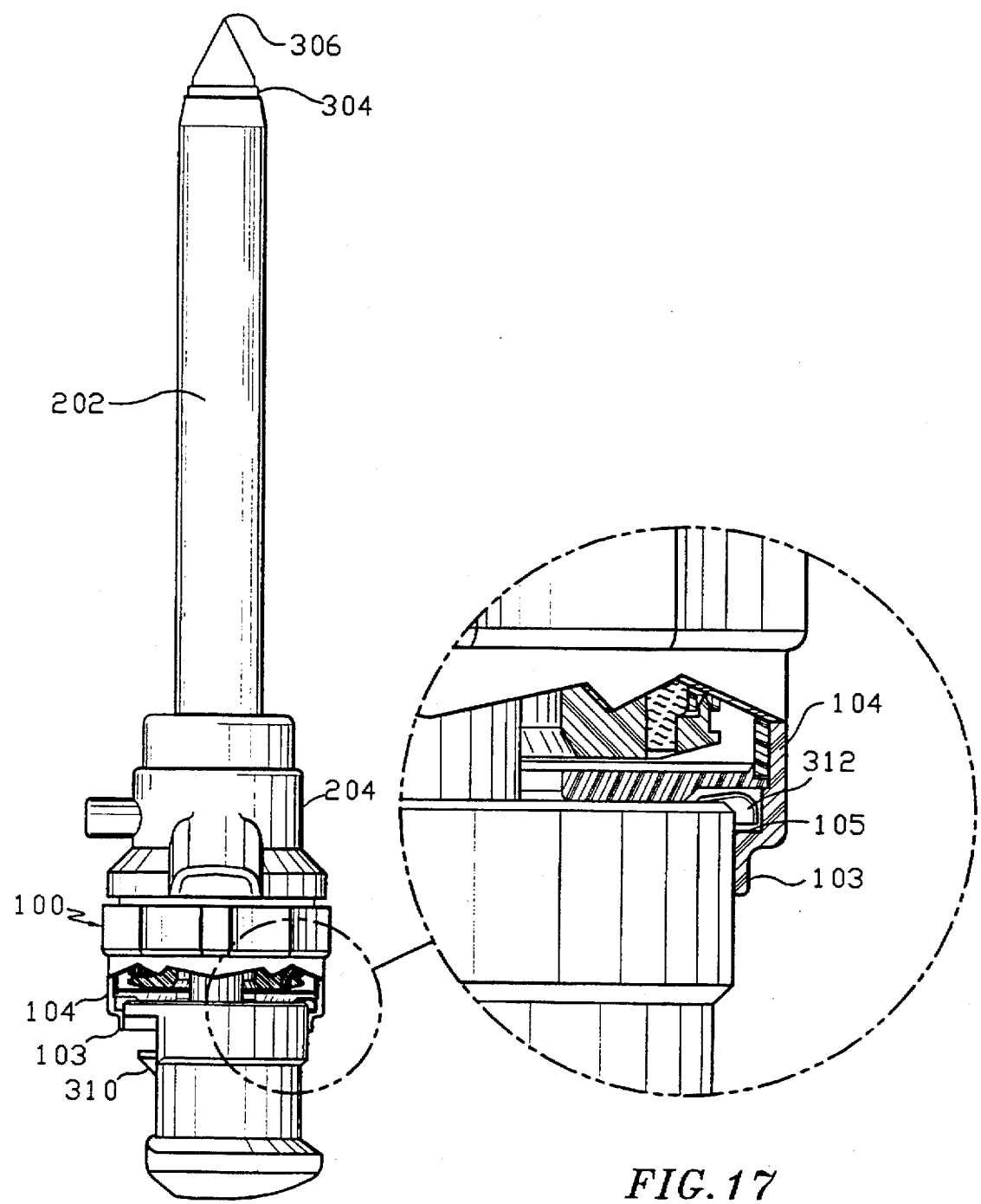
FIG. 16 is a side plan view in partial cross-section of an assembled trocar and cannula assembly in combination with the valve assembly of FIG. 2A.
FIG. 17 is an enlarged isolated view of the mechanism for detachably securing the trocar assembly relative to the valve assembly.

Referring now to FIGS. 1, 16 and 17, the novel valve assembly 100 may be used with a trocar of the type described in the figures. This trocar 300 is disclosed in U.S. patent application. Ser. No. 07/957,673 filed Oct. 7, 1992, now issued as U.S. Pat No. 5,356,241 the contents of which are incorporated herein by reference, and includes trocar housing 302, an obturator 304 extending distally from the housing 302 and having piercing tip 306 and a stationary or tube 308 which houses the obturator when it is unarmed. Obturator 304 is advanced beyond the distal end of sleeve 202 to expose the obturator tip 306 by advancing actuating button 310. This trocar 300 also includes a locking hinge 312 within the trocar housing 302 which is actuated upon depression of the actuating lever 310.

The trocar housing 302 may be longitudinally fixed relative to valve assembly 100 and cannula 200 by inserting the trocar within the aperture defined in end cap 102 of the assembly 100, advancing the trocar through the valve assembly and into cannula sleeve 202, and advancing actuating button 310. The proximal end portion 103 of end cap 102 defines a smaller diameter than the remaining or main portion of the cap 102 (See also FIG. 11) and, thus, defines a circumferential locking ledge 105 at its intersection with the main cap portion. Once the trocar 300 is appropriately positioned in the cannula sleeve 202, the obturator 304 and obturator tip 306 are advanced by advancing actuating button 310 which causes corresponding radial outward movement of the hinge member 312 and engagement of the hinge member 312 with the circumferential locking ledge 105 of the end cap 102 as shown in FIG. 17 to detachably secure the trocar housing 302 relative to the valve assembly 100 and cannula assembly 200. Because locking ledge 105 extends circumferentially, trocar housing 302 may be detachably secured to valve assembly 100 at any relative angular orientation. The valve assembly is capable of forming a seal about the trocar in the same manner described above.

In operation, the distal end of the trocar 300 having the obturator tip 306 in an exposed position beyond the sleeve 202 of the cannula assembly 200 is placed against the skin at the body cavity region, and pressure is exerted on the assembly against the skin. This pressure causes the obturator tip 306 to enter the skin and underlying tissue. Once the tip has penetrated the tissue and has entered the cavity, the tip automatically retracts into the cannula as described in U.S. Pat. No. 5,116,353, and the trocar can be withdrawn from the cannula assembly to permit introduction of surgical instruments such as forceps, graspers, or the like through the remaining cannula assembly 200. Alternatively, a trocar having a spring biased protective sleeve such as is described in U.S. Pat. No. 4,601,710 or a conventional trocar which does not include a safety mechanism may be employed through valve assembly 100 and cannula assembly 200. It is to be appreciated that upon removal of the trocar 300 from the cannula assembly 200, the duck bill 208 closes automatically to preserve the state of insufflation of the peritoneum. In particular, the pressure exerted by the insufflation gases through the cannula sleeve 202 biases the planar portions 214 (FIG. 14) of the duck bill 208 towards each other thereby closing the abutment face 216 defined at the juncture of the two planar portions.

Figure 18:
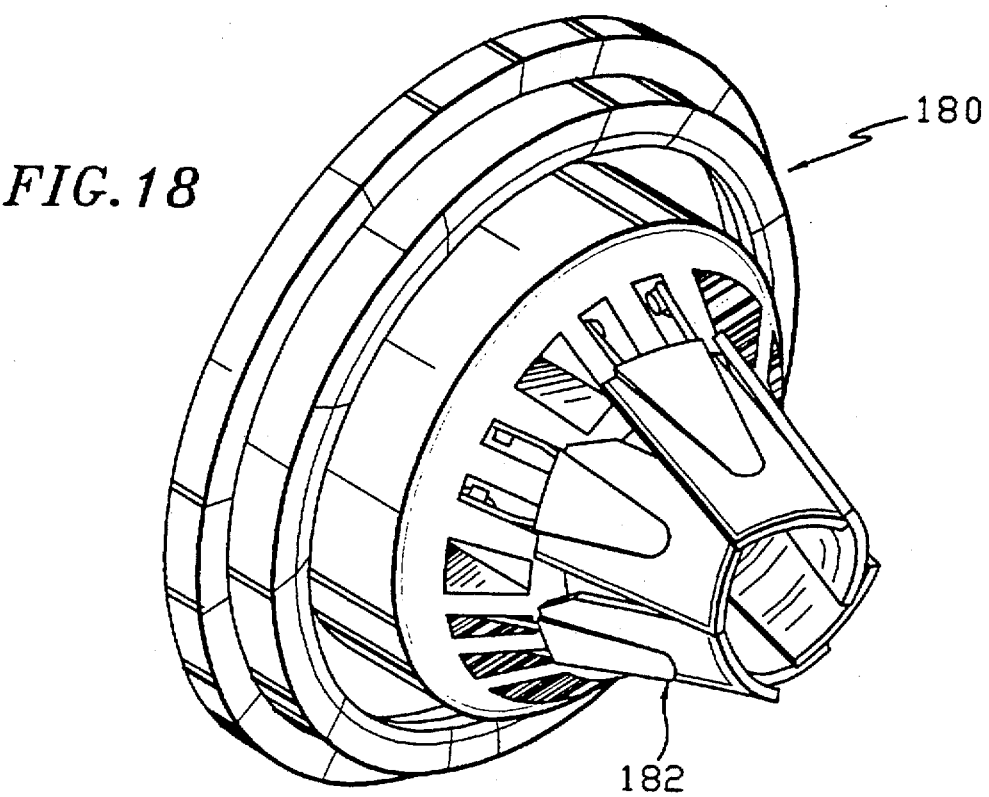
FIG. 18 is an enlarged perspective view of an alternative guard mount to be incorporated in the valve assembly of FIG. 2A.
Figure 19:
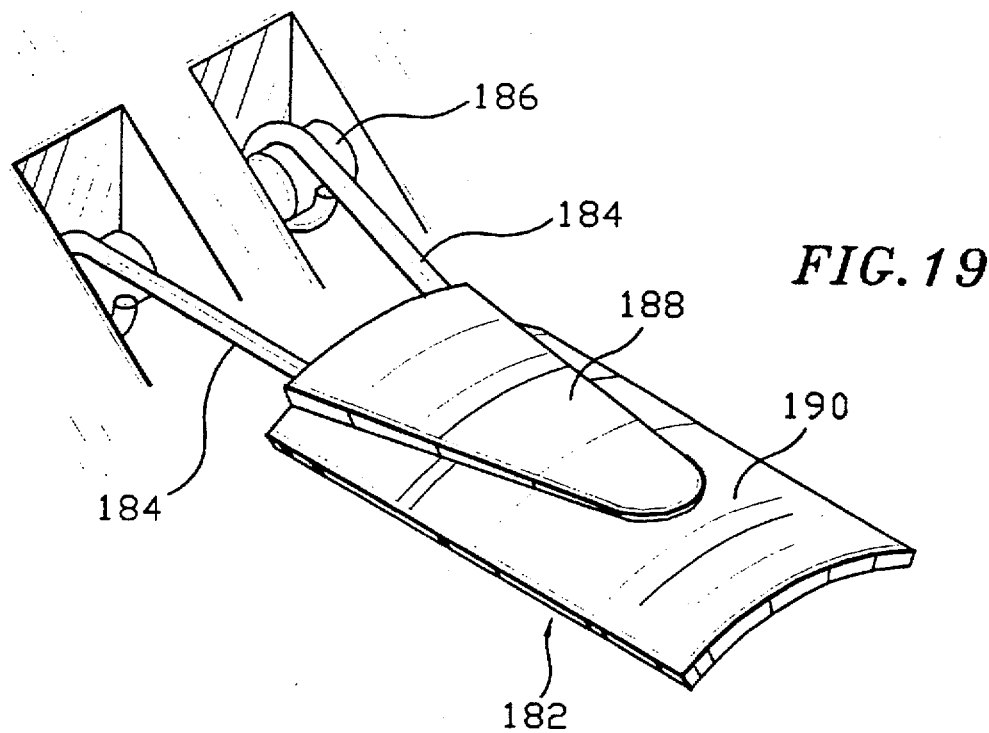
FIG. 19 is an enlarged perspective view of a single guard element of the guard mount of FIG. 18 illustrating the mounting of the guard element to the guard mount.
Figure 20:
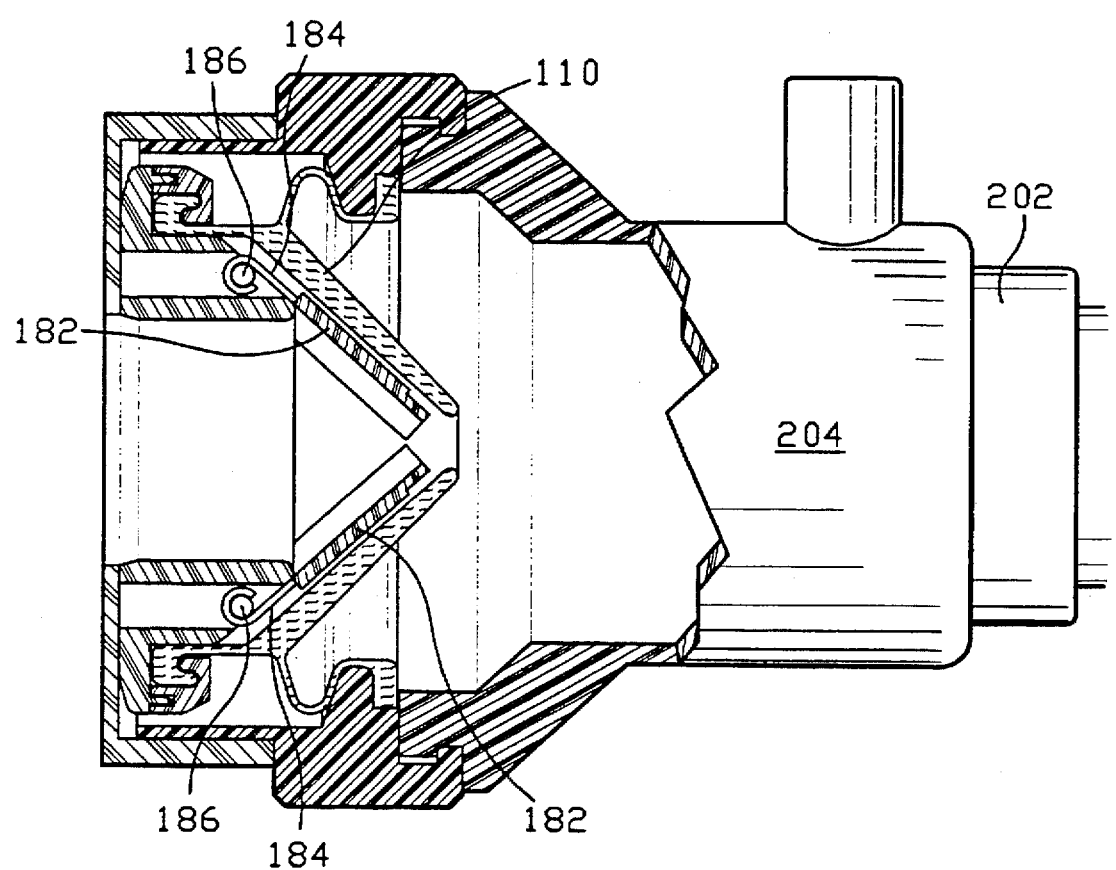
FIG. 20 is a cross-sectional view of the valve assembly with the guard mount of FIG. 18.

FIGS. 18–20 depict an alternate guard mount 180 to be incorporated in the valve assembly of the present disclosure. In accordance with this embodiment, the guard elements 182 are mounted to the guard mount via two rods 184 which are connected at their first ends to the guard element 182 via insert molding techniques and at the second ends to a pivot rod 186 within the guard mount. The guard elements 186 pivot in a similar manner to that described in connection with the embodiment of FIG. 1 and possess a rigid section as defined by the finger portion 188 and a more flexible outer section as defined by outer flap 190.

While the above description contains many specifics, these specifics should not be construed as limitations on the scope of the invention, but merely as an exemplification of a preferred embodiment thereof. Those skilled in the art will envision other possible variations that are within the scope and spirit of the invention as defined by the claims appended hereto.

What is claimed is:

1. Valve assembly for sealed reception of an elongated object, which comprises:
   a) a valve body having at least one opening configured and dimensioned to permit entry of an elongated object, and defining a central longitudinal axis;
   b) an elongated seal member formed of a resilient material and defining an aperture in general alignment with the opening of the valve body adapted to resiliently engage the outer surface of the object in a substantially fluid tight manner; and
   c) at least one elongated guard member disposed within the seal member and positioned to engage the elongated object upon at least partial insertion of the elongated object into the valve body, the guard member including at least a first substantially rigid portion and a second portion having less rigidity than the first portion, the guard member adapted to be displaced relative to the longitudinal axis such that at least the first substantially rigid member engages inner surface portions of the seal member proximal of the aperture to thereby facilitate expansion of the aperture of the seal member upon entry of the object therein.

2. The valve assembly according to claim 1 wherein the at least one guard member includes a plurality of guard members coaxially arranged about the central longitudinal axis.

3. The valve assembly according to claim 2 wherein the second portion of adjacent guard members are disposed in partial overlapping relation.

4. The valve assembly according to claim 3 wherein the guard members are mounted for pivotal movement.

5. The valve assembly according to claim 1 wherein the at least one guard member is mounted for pivotal movement relative to the longitudinal axis.

6. A valve assembly for sealed reception of an elongated object, which comprises:
   (a) a valve housing having a longitudinal opening configured and dimensioned to permit entry of an elongate object;

(b) an elongated resilient seal member at least partially positionable within the valve housing and defining an aperture to permit entry of the elongated object therein in at substantially fluid tight manner; and (c) a plurality of guard members disposed within the seal member and concentrically arranged about a central longitudinal axis defined by the valve housing and positioned to engage the elongated object upon insertion of the elongated object within the valve housing, the guard members arranged such that at least end portions of adjacent guard members are in overlapping relation, each guard member adapted to be radially displaced during introduction of the elongated object within the valve assembly to contact portions of the valve member adjacent, but proximal to, the aperture to facilitate passage of an elongated object therethrough, the end portions of the guard members being substantially flexible relative to the remaining portions of the guard members to effectively minimize force required to advance the elongated object through the guard members.

7. The valve assembly according to claim 6, further including a guard mount, wherein each guard member is movably mounted to the guard mount.

8. A valve assembly for sealed reception of an elongated object, which comprises:

(a) a valve housing having a longitudinal opening configured and dimensioned to permit entry of an elongated object; and (b) an elongated resilient seal member at least partially positionable within the valve housing, the seal member including an inner portion and a peripheral portion, and defining a central longitudinal axis, the inner portion defining a frusto conical configuration and having an aperture in general alignment with the central longitudinal axis to permit entry of the elongated object therein in a substantially fluid tight manner, the peripheral portion including a bellows structure characterized by extending in a longitudinal direction, the bellows structure in coaxial arrangement about at least a portion of the inner portion and being dimensioned to maintain a substantially fluid tight seal with the valve housing notwithstanding manipulation of the elongated object within the aperture in either a longitudinal or radial direction.

9. A valve assembly for sealed reception of an elongated object, which comprises:

(a) a valve housing having a longitudinal opening configured and dimensioned to permit entry of an elongated object;

(b) an elongated resilient seal member at least partially positionable within the valve housing, the seal member including an inner portion and a peripheral portion, and defining a central longitudinal axis, the inner portion defining a frusto conical configuration and having an aperture in general alignment with the central longitudinal axis to permit entry of the elongated object therein in a substantially fluid tight manner, the peripheral portion including a bellows structure characterized by extending in a general longitudinal direction, the bellows structure in coaxial arrangement about at least a portion of the inner portion and being dimensioned to maintain a substantially fluid tight seal with the valve housing notwithstanding manipulation of the elongated object within the aperture; and (c) at least two guard members disposed within the seal member and positioned to engage the elongated object upon passage through the longitudinal opening of the valve housing, the guard members having rigid portions characterized by having sufficient rigidity to engage an inner surface portion of the seal member proximal of the aperture to facilitate expansion of the aperture upon passage of the elongated object.

10. The valve assembly according to claim 9 including a plurality of guard members wherein adjacent guard members are disposed in partial overlapping arrangement.

* * * * *